United States Patent
Jordan et al.

(10) Patent No.: US 10,813,205 B2
(45) Date of Patent: Oct. 20, 2020

(54) DETECTING MOTION BY USING A LOW DOSE X-RAY IMAGE

(71) Applicant: Accuray Incorporated, Sunnyvale, CA (US)

(72) Inventors: Petr Jordan, Redwood City, CA (US); Jonathan Cecil Chappelow, Campbell, CA (US); Calvin R. Maurer, Jr., San Jose, CA (US); Eric Schnarr, McFarland, WI (US)

(73) Assignee: Accuray Incorporated, Sunnyvale, CA (US)

( * ) Notice: Subject to any disclaimer, the term of this patent is extended or adjusted under 35 U.S.C. 154(b) by 130 days.

(21) Appl. No.: 15/870,207

(22) Filed: Jan. 12, 2018

(65) Prior Publication Data
US 2019/0223278 A1 Jul. 18, 2019

(51) Int. Cl.
H05G 1/42 (2006.01)
A61N 5/10 (2006.01)
A61B 6/00 (2006.01)

(52) U.S. Cl.
CPC .............. *H05G 1/42* (2013.01); *A61B 6/463* (2013.01); *A61B 6/5229* (2013.01); *A61B 6/5264* (2013.01); *A61B 6/542* (2013.01); *A61B 6/582* (2013.01); *A61N 5/1037* (2013.01); *A61N 5/1049* (2013.01); *A61N 2005/1061* (2013.01)

(58) Field of Classification Search
CPC .................... A61B 6/032; A61B 6/488; A61N 2005/1061; A61N 5/1037; A61N 2005/1062; A61N 5/1039; G06T 2207/30004; G06T 7/0014
USPC ....... 382/128, 130, 131, 132, 170, 171, 289, 382/291, 293, 295, 302; 128/922, 923
See application file for complete search history.

(56) References Cited

U.S. PATENT DOCUMENTS

| | | | | |
|---|---|---|---|---|
| 6,496,557 | B2 * | 12/2002 | Wilson | A61B 6/06 250/370.09 |
| 7,519,160 | B2 * | 4/2009 | Vermeulen | A61B 5/0046 378/145 |
| 7,711,087 | B2 | 5/2010 | Mostafavi | |
| 7,792,245 | B2 * | 9/2010 | Hitzke | A61B 6/107 378/37 |
| 7,809,104 | B2 * | 10/2010 | Foland | G01V 5/0025 378/198 |
| 7,825,376 | B2 * | 11/2010 | Boyden | G01N 23/223 250/305 |

(Continued)

OTHER PUBLICATIONS

Gray et al., "Reference Values for Diagnostic X-Ray Examinations," Report of AAPM Task Group No. 7, Radiology 235(2): 354-358, May 2005.

(Continued)

*Primary Examiner* — Yosef Kassa
(74) *Attorney, Agent, or Firm* — Womble Bond Dickinson (US) LLP

(57) ABSTRACT

A reference image of a patient may be generated. A subsequent x-ray image of the patient may be generated after the generating of the reference image where the subsequent x-ray image is associated with a low dosage. A difference between the reference image and the subsequent x-ray image that is associated with the low dosage may be determined. A motion of the patient may be identified as having occurred based on the determined difference.

26 Claims, 10 Drawing Sheets

(56) References Cited

U.S. PATENT DOCUMENTS

| | | | | |
|---|---|---|---|---|
| 7,840,046 B2* | 11/2010 | Jerebko | ............... | G06T 11/005 |
| | | | | 382/128 |
| 7,924,969 B2* | 4/2011 | Yamakawa | ............ | A61B 6/032 |
| | | | | 378/5 |
| 8,306,303 B2* | 11/2012 | Bruder | ................... | A61B 6/481 |
| | | | | 382/131 |
| 8,463,012 B2* | 6/2013 | Rauch | ...................... | G06T 7/38 |
| | | | | 378/4 |
| 8,553,959 B2* | 10/2013 | Hsieh | ..................... | A61B 6/037 |
| | | | | 382/131 |
| 8,559,596 B2* | 10/2013 | Thomson | .............. | G06T 7/0014 |
| | | | | 378/65 |
| 8,718,346 B2* | 5/2014 | Isaacs | ..................... | G06T 11/60 |
| | | | | 382/131 |
| 8,971,996 B2* | 3/2015 | Flohr | ..................... | A61B 6/541 |
| | | | | 600/428 |
| 2007/0025509 A1 | 2/2007 | Pang et al. | | |
| 2009/0296886 A1 | 12/2009 | Maltz et al. | | |
| 2011/0135051 A1 | 6/2011 | Fadler et al. | | |

OTHER PUBLICATIONS

Accuray Incorporated, "Estimation of the Imaging Dose for the CyberKnife® Robotic Radiosurgery System," Sunnyvale, CA, 2013, white paper 500733.B, published 2013.

\* cited by examiner

DETECTING MOTION BY USING A LOW DOSE X-RAY IMAGE

TECHNICAL FIELD

The present disclosure relates to x-ray images, and more specifically, relates to detecting motion by using a low dose x-ray image.

BACKGROUND

An x-ray image may be used to identify a feature of a patient. For example, the patient may be positioned so that an x-ray imager may expose the patient to a dosage of radiation and to generate the x-ray image. The image quality of the x-ray image may be based on the dosage of the radiation that is exposed to the patient. For example, the image quality of a higher dosage x-ray image may be superior to the image quality of a lower dose x-ray image.

BRIEF DESCRIPTION OF THE DRAWINGS

The present disclosure will be understood more fully from the detailed description given below and from the accompanying drawings of various implementations of the disclosure.

DETAILED DESCRIPTION

Figure 1:
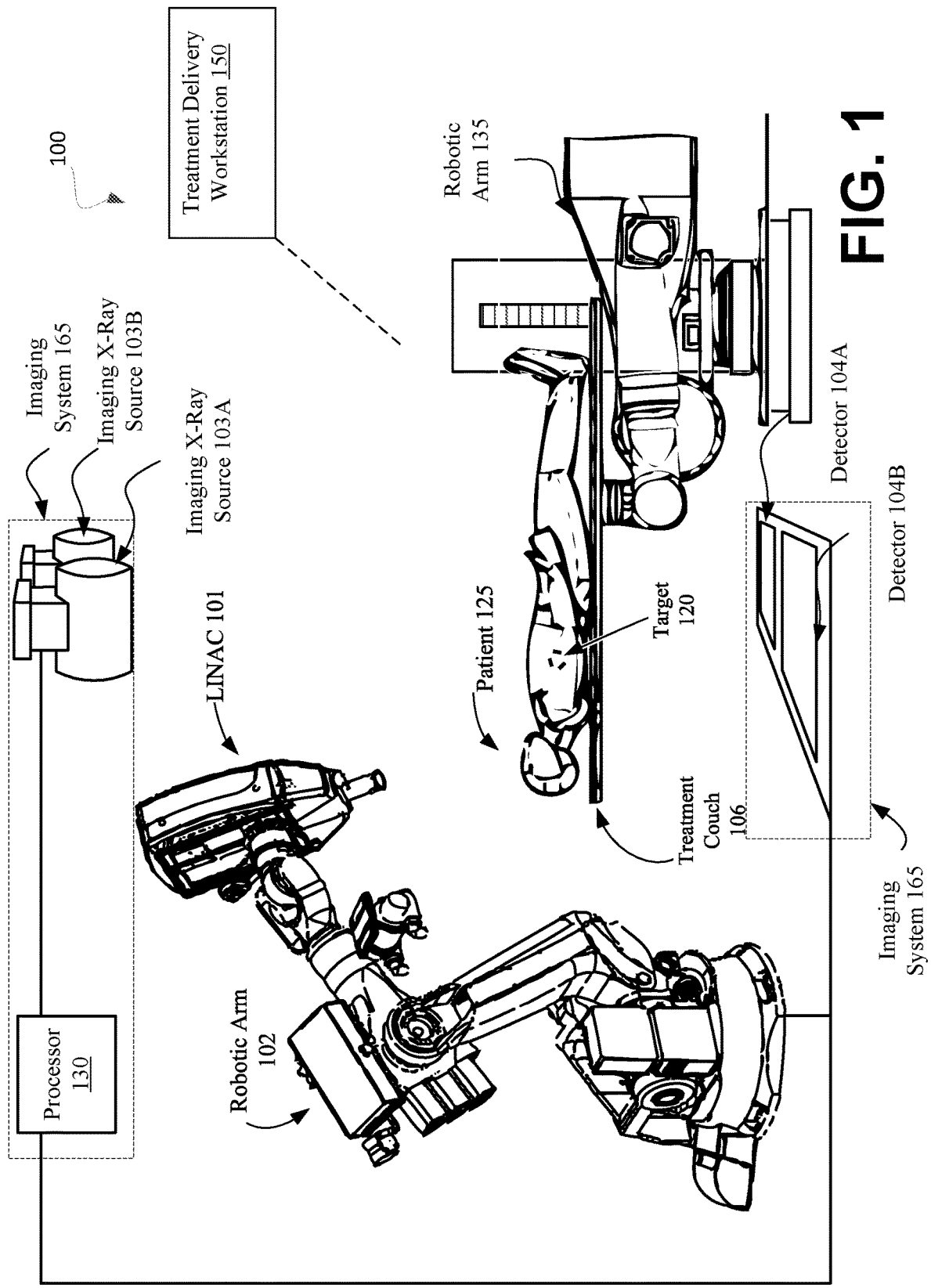
FIG. 1 illustrates a radiation treatment system in accordance with embodiments of the present disclosure.

Aspects of the present disclosure relate to detecting a target motion of a patient based on a difference between a lower dose x-ray image and a reference image. A treatment delivery (e.g., radiation treatment delivery) may be performed on the patient. For example, a dose of radiation may be delivered to a target (e.g., a tumor) of the patient that is located in a target region of the patient.

The tracking of the target may be used to focus the dose of radiation to the target of the patient so that radiation is focused on the location of the target as opposed to healthy portions of the patient. During the treatment delivery, the patient may be subjected to an unexpected movement or shift (e.g., a patient couch inadvertently rotating) so that the location of the target region of the patient deviates from a prior location during the treatment delivery. Such an unexpected movement may result in the dose of radiation being delivered to the healthy portion of the patient as opposed to the target region of the patient that includes the tumor.

Images of the patient may be used to detect the unexpected movement of the patient during the treatment delivery. For example, x-ray images of the patient may be used to detect that the patient has unexpectedly moved or shifted. A reference x-ray image may be taken of the patient at the start of the treatment delivery when the patient is properly positioned so that the dose of radiation is applied to the target region. As the treatment delivery is performed, subsequent x-ray images may be taken of the patient and each subsequent x-ray image may be compared with the reference x-ray image to identify whether the patient has moved or shifted so that the target region is no longer being accurately provided the dose of radiation. In response to identifying that the patient has moved or shifted, the treatment delivery may be altered based on the new position of the patient so that the dose of radiation may be accurately provided to the target region.

The use of x-ray images to track the target region and identify the movement or shift of the patient may use high dosage x-ray images where an energy of an x-ray imaging beam may be increased and expose the patient to unnecessary and additional radiation. For example, multiple higher dosage x-ray images of the patient may be obtained and a difference between a first higher dosage x-ray image and a second higher dosage x-ray image may be used to identify whether the patient has moved. However, for certain portions of the body of a human patient, repeated higher dosage x-ray images may not be needed to detect the movement or shift of the patient during treatment delivery. For example, the movement or shift of the patient may be detected from lower dosage x-ray images of the head or spine (or other such features) of the patient during treatment delivery. A higher dosage x-ray image of the patient at the start of the treatment delivery may be obtained and subsequent lower dosage x-ray images of the patient may be obtained periodically during treatment delivery. Thus, lower dose x-ray images may be generated at time periods after a prior lower dose x-ray image has been generated. The lower dosage x-ray images may be normalized relative to the higher dosage x-ray image. For example, the pixel intensity values for the lower dosage x-ray images may be modified to match a distribution of pixel intensity values for the higher dosage x-ray image. Subsequently, a difference between the modified lower dosage x-ray image and the higher dosage x-ray image may indicate that the patient has unexpectedly moved or shifted so that the treatment delivery may no longer be accurate relative to the target region of the patient.

A workflow to provide the treatment delivery (e.g., a radiation treatment) to a patient may involve multiple stages corresponding to treatment planning, patient setup, and treatment delivery. The treatment planning may be the first stage to provide radiation treatment to the patient. For example, the treatment planning stage may be initiated by the obtaining of pre-treatment diagnostic images with one or more imaging modalities (e.g., computerized tomography (CT) image, magnetic resonance imaging (MRI) scan, etc.)

of a target region of the patient. The treatment planning stage may further include identifying one or more reference points in one or more of the pre-treatment images (e.g., a reference x-ray image of a higher dosage). The reference points may be one or more imageable landmarks or points of interest (e.g., contours of the skull of spine) in the acquired images that can be tracked during later stages as discussed below. The acquired images in the treatment planning stage such as a CT image includes a pathological anatomy that is targeted for treatment, and well as a critical region(s) that is positioned near the pathological anatomy. Treatment planning software enables the generation of a critical region contour around the critical region and a target region contour around the pathological anatomy. Conventionally, a user manually delineates or uses a software tool to auto-delineate points on a display that is used by the treatment planning software to generate the corresponding contours. After the target has been defined, the critical and soft tissue volumes have been specified, and minimum radiation dose to the target and the maximum dose to normal and critical healthy tissue has been specified, the treatment planning software then produces a treatment plan, relying on the positional capabilities of the radiation treatment system.

The second stage of the workflow may correspond to a patient setup before providing the radiation treatment to the patient. An alignment image may be generated, such as by X-ray imaging, or a 3D alignment image may be generated, such as a cone-beam CT (CBCT) or a megavoltage CT (MVCT) image, and then correlated to the preoperative image in order to locate the target region accurately. Then, a radiation source located on treatment delivery system (e.g., a linear accelerator (LINAC)) is automatically positioned based on the correlation between the preoperative image and the alignment image in order to accurately target the desired treatment region in the patient. If the patient is not within a desired range of the radiation treatment delivery, the position of the patient may be adjusted during the patient setup stage.

After the patient setup stage, treatment delivery may be performed on the patient based on the treatment plan. During treatment delivery, dynamic tracking of the target may be performed based on the use of x-ray images taken to identify internal features of the patient to track motions of the target (e.g., due to respiration or other such movement) with the registration results between a digitally reconstructed radiograph (DRR) and each of the live x-ray images used to generate a correlation model. Once the location of the target (e.g., the tumor) has been computed, the radiation beam source position of the radiation treatment delivery system may be adjusted to compensate for the dynamic motion of the target. The radiation treatment delivery system may then deliver the dose of radiation to the tracked target in accordance with the radiation treatment plan developed during the treatment planning stage. However, if the patient unexpectedly shifts or moves, then the position of the target region of the patient may not be in accordance with the treatment plan that positions the radiation beam source.

Aspects of the present disclosure identify the unexpected shift or movement of the patient so that the treatment delivery may be adjusted to account for the unexpected shift or movement while reducing the total amount of radiation exposure to the patient. For example, the reference image may be an x-ray image that is of a higher dosage. The higher dose reference image may be of a feature of the patient and may correspond to a higher quality (e.g., less noise) image of the patient. Subsequent x-ray images of a lower dosage of a lower quality (e.g., with more noise than the higher dose) may be obtained of the patient where the subsequent x-ray images are of a lower dosage. The lower dose subsequent x-ray images may be registered to the reference image to identify whether the patient has unexpectedly shifted or moved during treatment delivery. For example, a difference between the reference image and the lower dose subsequent x-ray image may indicate that the patient has unexpectedly shifted or moved. In response to identifying that the patient has unexpectedly shifted or moved, an imager that is used to generate the x-ray images may be adjusted from generating the lower dose x-ray images to generating a higher dose x-ray image that is then compared with the reference image to determine an amount of the motion. Furthermore, the treatment delivery may subsequently be adjusted based on the amount of the motion that has been detected.

As such, the present disclosure may reduce the amount of radiation exposed to a patient by adjusting the delivery of the dose of radiation when a patient unexpected moves or shifts during treatment delivery and by reducing the number of higher dosage x-ray images that may be taken of the patient. Although aspects of the present disclosure describe a radiation treatment delivery system, any type of treatment delivery system may be used with the present disclosure. For example, a treatment delivery system that accurately delivers a treatment to a target region of a patient in order to avoid damaging healthy portions of the patient may be based on the present disclosure. For example, other types of medical procedures of treatment delivery may include, but are not limited to, positioning of biopsy needles, ablative, ultrasound or other focused energy treatments, positioning a laser beam for a laser beam treatment or positioning radioactive seeds for brachytherapy, etc. Prior to describing the present disclosure, an example radiosurgery device will be described to provide a better understanding of the present disclosure.

FIG. 1 illustrates a radiation treatment system 100. The radiation treatment system 100 may be used to deliver a radiation treatment by detecting a target motion based on a difference between a lower dose x-ray image and a higher dose x-ray image.

As shown, FIG. 1 illustrates a configuration of a radiation treatment system 100. In the illustrated embodiments, the radiation treatment system 100 includes a linear accelerator (LINAC) 101 that acts as a radiation treatment source. In one embodiment, the LINAC 101 is mounted on the end of a robotic arm 102 having multiple (e.g., 5 or more) degrees of freedom in order to position the LINAC 101 to irradiate a pathological anatomy (e.g., target 120) with beams delivered from many angles, in many planes, in an operating volume around a patient. Treatment may involve beam paths with a single isocenter, multiple isocenters, or with a non-isocentric approach. Alternatively, other types of image guided radiation treatment (IGRT) systems may be used. In one alternative embodiment, the LINAC 101 may be mounted on a gantry based system to provide isocentric beam paths.

In one embodiment, the LINAC 101 may be positioned at multiple different nodes (predefined positions at which the LINAC 101 is stopped and radiation may be delivered) during treatment by moving the robotic arm 102. At the nodes, the LINAC 101 can deliver one or more radiation treatment beams to a target. The nodes may be arranged in an approximately spherical distribution about a patient. The particular number of nodes and the number of treatment beams applied at each node may vary as a function of the location and type of pathological anatomy to be treated.

Referring to FIG. 1, the radiation treatment system 100 may include an imaging system 165 having a processor 130 connected with x-ray sources 103A and 103B (i.e., imaging sources) and fixed x-ray detectors 104A and 104B. Alternatively, the x-ray sources 103A, 103B and/or x-ray detectors 104A, 104B may be mobile, in which case they may be repositioned to maintain alignment with the target 120, or alternatively to image the target from different orientations or to acquire many x-ray images and reconstruct a three-dimensional (3D) cone-beam CT. In one embodiment, the x-ray sources are not point sources, but rather x-ray source arrays, as would be appreciated by the skilled artisan. In one embodiment, LINAC 101 serves as an imaging source, where the LINAC power level is reduced to acceptable levels for imaging.

Imaging system 165 may perform computed tomography (CT) such as cone beam CT or helical megavoltage computed tomography (MVCT), and images generated by imaging system 165 may be two-dimensional (2D) or three-dimensional (3D). The two x-ray sources 103A and 103B may be mounted in fixed positions on the ceiling of an operating room and may be aligned to project x-ray imaging beams from two different angular positions (e.g., separated by 90 degrees) to intersect at a machine isocenter (referred to herein as a treatment center, which provides a reference point for positioning the patient on a treatment couch 106 during treatment) and to illuminate imaging planes of respective detectors 104A and 104B after passing through the patient. In one embodiment, imaging system 165 provides stereoscopic imaging of the target 120 and the surrounding volume of interest (VOI). In other embodiments, imaging system 165 may include more or less than two x-ray sources and more or less than two detectors, and any of the detectors may be movable rather than fixed. In yet other embodiments, the positions of the x-ray sources and the detectors may be interchanged. Detectors 104A and 104B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with a reference image during an image registration process that transforms a coordinate system of the digital image to a coordinate system of the reference image, as is well known to the skilled artisan. The reference image may be, for example, a digitally reconstructed radiograph (DRR), which is a virtual x-ray image that is generated from a 3D CT image based on simulating the x-ray image formation process by casting rays through the CT image.

As shown in FIG. 1, the image-guided radiation treatment system 100 may further be associated with a treatment delivery workstation 150. The treatment delivery workstation may be remotely located from the radiation treatment system 100 in a different room that the treatment room in which the radiation treatment system 100 and patient are located. The treatment delivery workstation 150 may include a processing device and memory that modify a treatment delivery to the patient 125 based on a detection of a target motion that is based on a difference between a lower dose x-ray image and a higher dose x-ray image as described below.

In some embodiments, a gantry system with a helical delivery may be used to rotate the imaging system 165. For example, the gantry system may be used to acquire two, three, or more images (e.g., x-ray images) at different angles.

Figure 2:
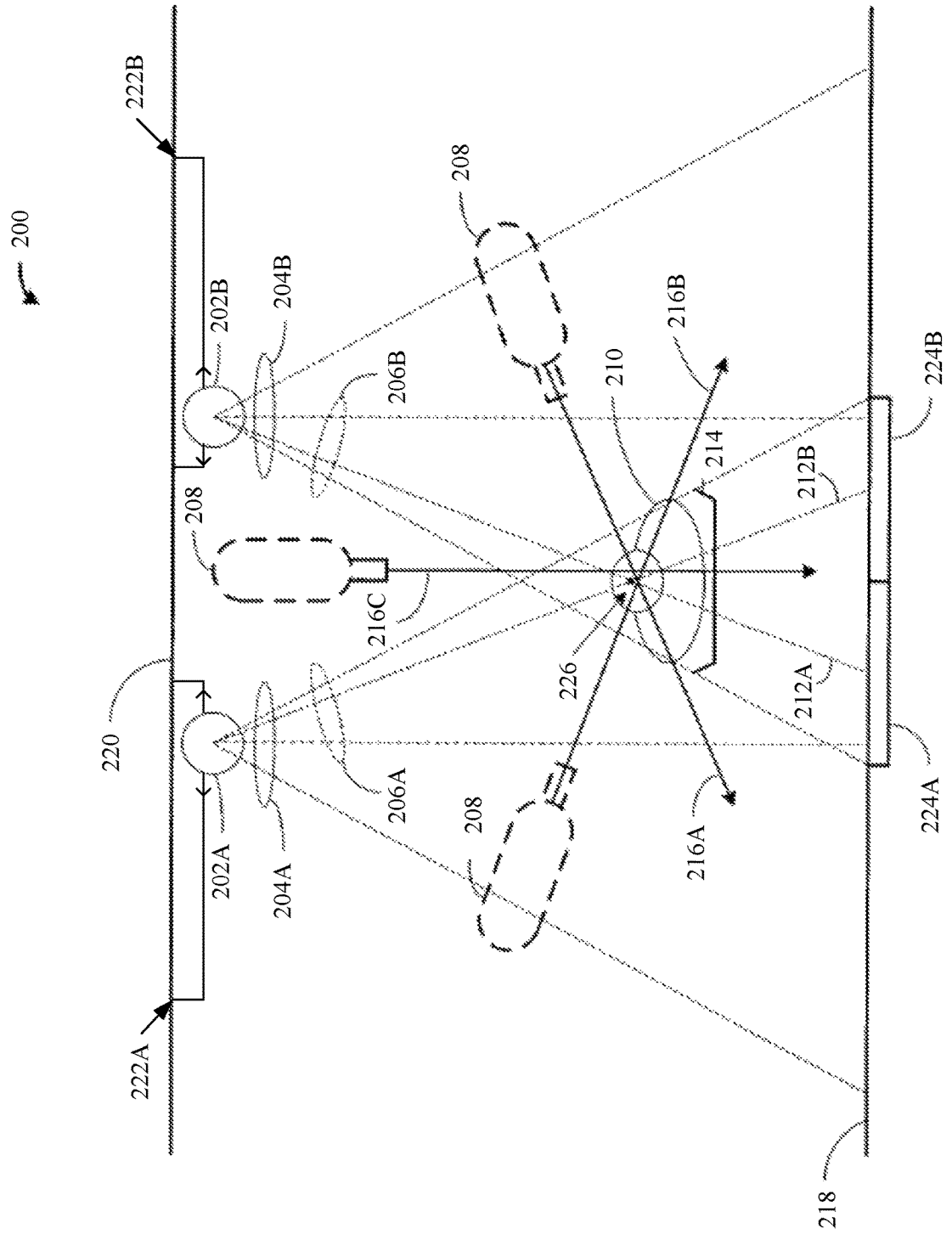
FIG. 2 is a cross-section of the radiation treatment system in accordance with some embodiments.

FIG. 2 illustrates the configuration of an image-guided radiation treatment (IGRT) system 200. In general, the IGRT system 200 may correspond to the radiation treatment system 100 of FIG. 1.

As shown in FIG. 2, the IGRT system 200 may include to kilovoltage (kV) imaging sources 202A and 202B that may be mounted on tracks 222A and 222B on the ceiling 220 of an operating room and may be aligned to project imaging x-ray beams 204A and 204B from two different positions such that a ray 212A of beam 204A intersects with a ray 212B of beam 204B at an imaging center 226 (i.e., isocenter), which provides a reference point for positioning the LINAC 208 to generate treatment beams 216A, 216B and 216C and the patient 210 on treatment couch 214 during treatment. After passing through the patient 210, imaging x-ray beams 204A and 204B may illuminate respective imaging surfaces of x-ray detectors 224A and 224B, which may be mounted at or near the floor 218 of the operating room and substantially parallel to each other (e.g., within 5 degrees). The kV imaging sources 202A and 202B may be substantially coplanar such that the imaging surfaces of kV imaging sources 202A and 202B form a single imaging plane. In one embodiment, kV imaging sources 202A and 202B may be replaced with a single kV imaging source. Once an x-ray image of the patient 214 has been generated, the LINAC 208 may rotate to generate a treatment beam 216 from a different angle. While the LINAC 208 rotates to the different angle, the kV imaging sources 202A and 202B may move along tracks 222A and 222B to generate x-ray images of the patient 210 from a new angle.

Figure 3:
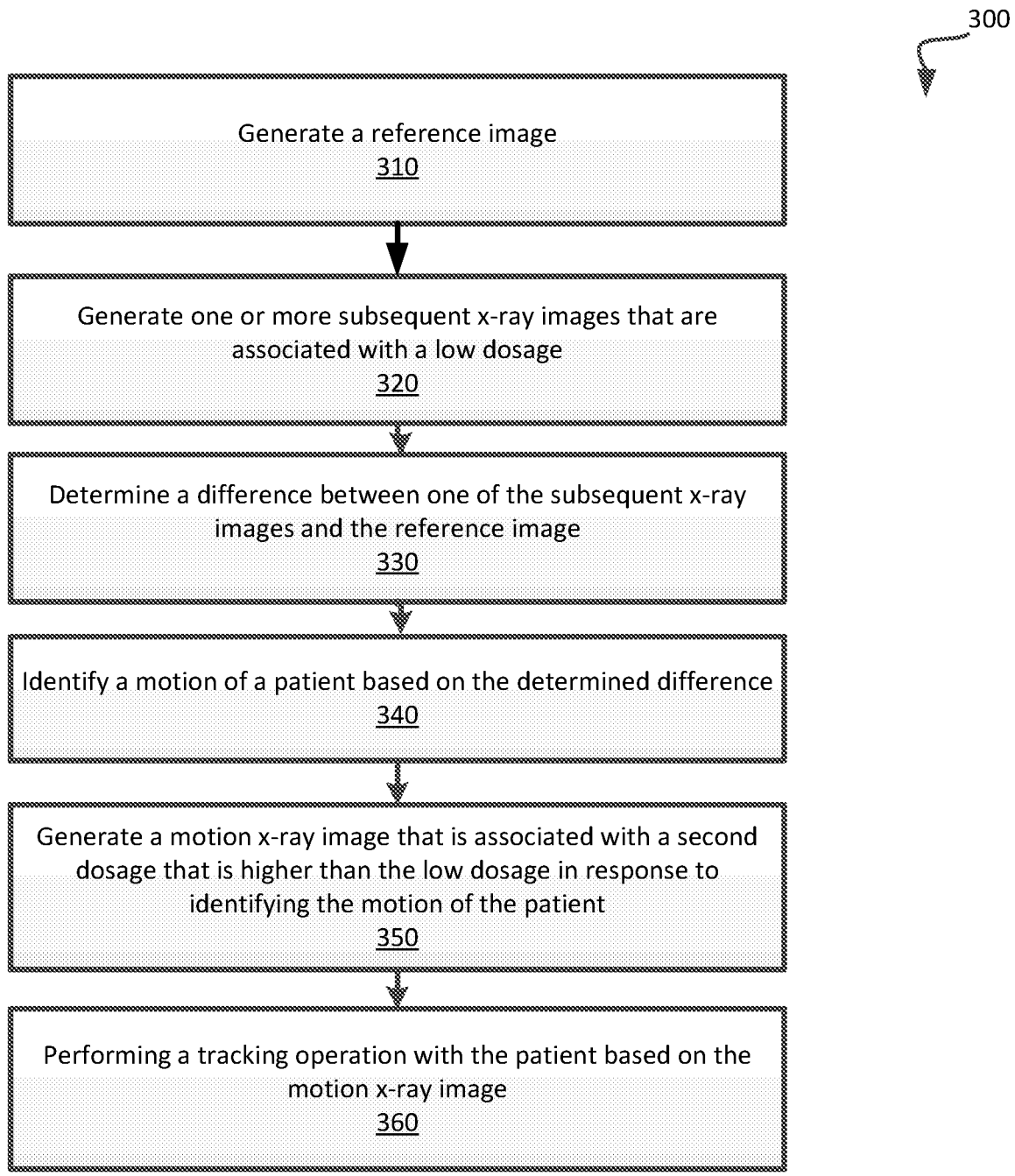
FIG. 3 is a flowchart of an example method to detect a motion associated with a target region based on low dosage x-ray images in accordance with embodiments of the present disclosure.

FIG. 3 is a flowchart of an example method 300 to detect a motion associated with a target region based on lower dosage x-ray images. In general, the method 300 may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the method 300 may be performed by processing logic of the radiation treatment system 100 of FIG. 1.

As shown in FIG. 3, the method 300 may begin with the processing logic generating a reference x-ray image (block 310). For example, an x-ray imager may be calibrated or configured to generate the reference x-ray image. In some embodiments, the reference image may be an x-ray image of a higher dosage than a subsequent x-ray image as described below or the reference image may be a Digitally Reconstructed Radiograph (DRR) image. The processing logic may generate one or more subsequent x-ray images that are associated with a low radiation dosage (block 320). The low radiation dosage may be lower than the higher dosage associated with the reference image when the reference image is an x-ray image. For example, the x-ray imager may be recalibrated or reconfigured to generate the subsequent x-ray images at a lower dosage relative to the higher dosage of the reference x-ray image. Thus, the subsequent x-ray images may be of a lower dosage relative to the reference x-ray image. For example, the subsequent x-ray images may be between 5 times to 80 times of a lower dosage than the reference x-ray image.

In one embodiment, an x-ray imaging technique for tracking the head uses 105-125 kV x-ray tube voltage and 10 mAs tube current-exposure time product (e.g., 100 mA tube current and 100 ms exposure time). The entrance skin dose per single image, which may be defined as air kerma measured at the imaging center, for 120 kV and 10 mAs imaging technique may be approximately 0.18 mGy. The use of entrance air kerma for planar x-ray imaging may conform to the AAPM convention for defining reference dose values for diagnostic radiology. Examples of low-dose x-ray imaging techniques may be 60 kV and 10 mAs (e.g., 100 mA, 100 ms), which may have approximately 0.040 mGy (e.g., 4.5 times dose reduction); 60 kV and 2.5 mAs (e.g., 50 mA, 50 ms), which may have approximately 0.008 mGy (e.g., 22 times dose reduction); and 60 kV and 0.4 mAs (e.g., 8 mA, 50 ms), which may have approximately 0.002 mGy (e.g., 90 times dose reduction).

In some embodiments, the image quality of the lower dosage x-ray image may only need to be sufficient to determine whether the motion associated with the target region of a patient has occurred in two consecutive x-ray images. Thus, the lower dosage may be based on such a dosage that is used to acquire an x-ray image at the sufficient image quality.

The processing logic may further determine a difference between one of the subsequent x-ray images and the reference x-ray image (block 330). For example, multiple lower dosage subsequent x-ray images may be taken where each of the lower dosage x-ray images are obtained periodically after the reference image has been obtained. A difference between normalized pixel intensity values between one of the subsequent x-ray images and the reference image may indicate that the patient has unexpectedly moved or shifted during treatment delivery. For example, a similarity measure between the subsequent x-ray image and the reference image may be obtained. Further details with regards to determining a difference between one of the subsequent x-ray images and the reference image are described in conjunction with FIG. 5.

Referring to FIG. 3, the processing logic may further identify a motion of a patient based on the determined difference between the subsequent x-ray image and the reference image (block 340). In some embodiments, the motion of the patient may be identified based on the determined difference between the subsequent and reference images exceeding a threshold difference or a similarity value threshold. Furthermore, the threshold difference may be defined during the treatment planning stage for the treatment delivery and/or may be based on a type of clinical scenario (e.g., type of treatment for the patient) associated with the treatment delivery. The threshold difference or similarity value threshold may be different based on the type of clinical scenario or based on the portion of the body that is observed in the x-ray images. For example, a first similarity measure threshold may be used to identify whether the patient has shifted or moved when the subsequent and reference images include the skull of the patient and a second similarity measure threshold may be used to identify whether the patient has shifted or moved when the subsequent and reference images include the spine of the patient where the first and second threshold thresholds are at different values. The similarity measure threshold may be different for other portions of the patient that are subjected to the x-ray images or for different clinical scenarios.

The processing logic may subsequently generate a motion x-ray image that is associated with a second radiation dosage that is higher than the low dosage in response to identifying the motion of the patient (block 350). For example, the motion x-ray image may be of the same dosage as a reference x-ray image that was obtained prior to the obtaining of the subsequent x-ray images. Thus, the x-ray imager may be recalibrated or reconfigured to generate the motion x-ray image at a higher dosage relative to the subsequent x-ray images that were being periodically obtained. In some embodiments, multiple imagers may be used to obtain the x-ray images. As such, multiple imagers may be configured to generate the x-ray images. Thus, in response to detecting the motion of the patient, a full-dose (e.g., higher dose) x-ray image (or pair of images) may be obtained and used to estimate an amount of the motion. The processing logic may further perform a tracking operation with the patient based on the motion x-ray image (block 360). For example, the motion x-ray image may be compared with the reference x-ray image of the same dosage to determine an amount that the patient has moved or shifted. In some embodiments, the motion x-ray image may be compared with a Digitally Reconstructed Radiograph (DRR) image. The tracking operation may correspond to an image registration of the motion x-ray image with the reference x-ray image or the reference DRR image. For example, a transformation between the motion x-ray image and the reference image may be obtained to estimate a spatial transformation between the reference image and the motion x-ray image. Subsequently, a medical procedure may be modified by using the transformation. For example, a medical procedure may be stopped or a treatment of the medical procedure may be altered based on the transformation or difference between the reference image and the motion x-ray image.

Thus, after detecting a motion of a patient by comparing a lower dosage x-ray image with a higher dosage x-ray image, a tracking operation using lower dosage x-ray images that are compared with the higher dosage x-ray image may be changed to comparing higher dosage x-ray images with each other or with a DRR image. Thus, if an episodic or other such motion of the patient is detected, a full dose x-ray image (or pair of x-ray images) may be quickly acquired to estimate the amount of the motion.

Figure 4:
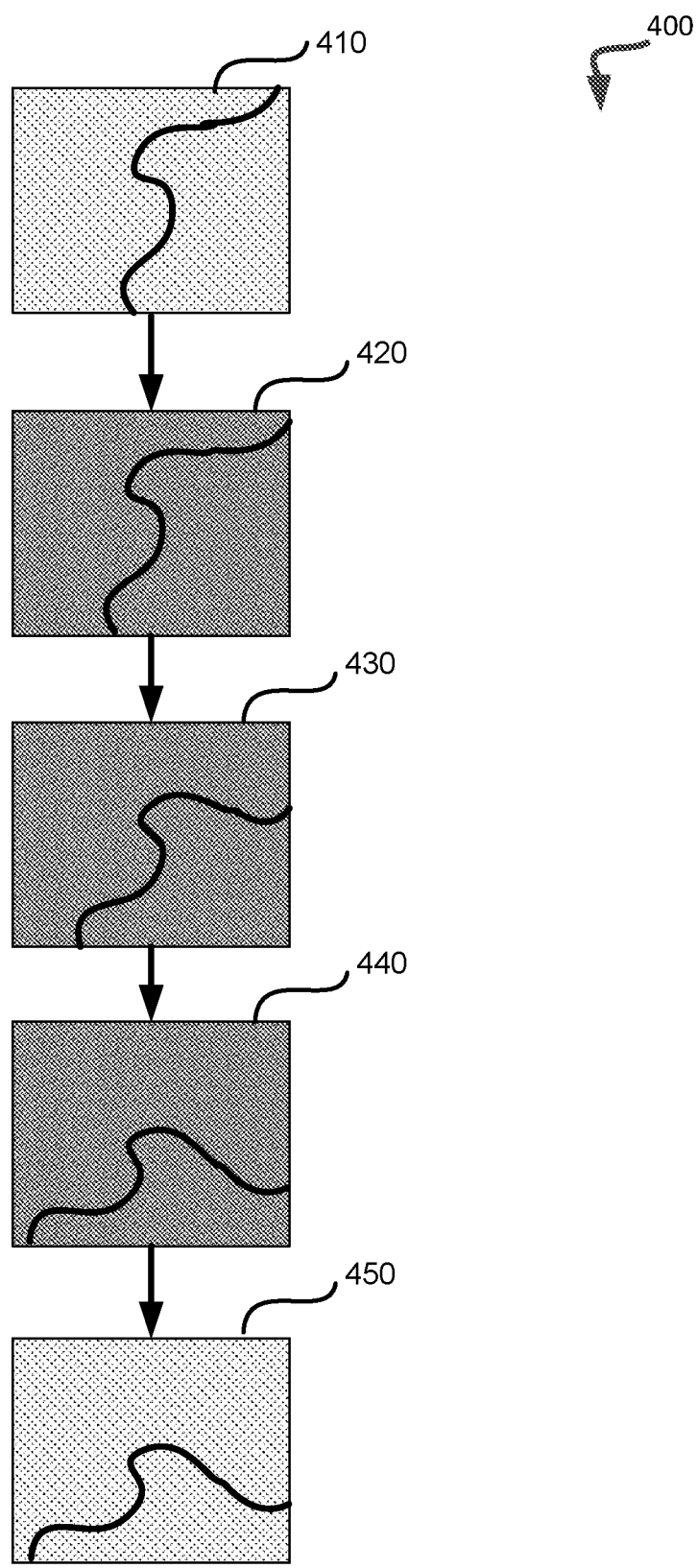
FIG. 4 is an illustration of an example sequence of images to detect a motion associated with a target region in accordance with some embodiments.

FIG. 4 is an illustration of an example sequence 400 of images to detect a motion associated with a target region of a patient. In general, the x-ray images of the sequence 400 may be obtained by the radiation treatment system 100 of FIG. 1.

As shown in FIG. 4, the sequence 400 may include multiple images. For example, a first image 410 may be obtained at a first time at the start of treatment delivery for the patient. The first image 410 may be an x-ray image taken at a higher dosage reference x-ray image that includes a feature of the patient (e.g., a skull contour or spinal contour) or may be a DRR image of the patient. While the patient is underdoing the treatment delivery, subsequent x-ray images of a lower dosage may be obtained of the patient as previously described. For example, a second x-ray image 420 may be obtained at a time after the first image 410 has been obtained. As shown, the second x-ray image 420 may have a higher amount of noise than the first image 410. The second x-ray image 420 may not indicate a motion of the patient based on a difference between the first image 410 and the second x-ray image 420. For example, features of the patient (e.g., the contours of a skull) may not have changed positions since the first image 410 was obtained. Subsequent x-ray images may be obtained at periodic intervals. For example, the third x-ray image 430 may be obtained after the second x-ray image 420. As shown, the third x-ray image 430 may indicate a motion of the patient based on a difference between the third x-ray image 430 and the first x-ray image 410. For example, a difference that does not exceed a threshold difference (or a similarity measure threshold value) may be identified. Since the difference does not exceed the threshold difference, a higher dosage x-ray image may not be obtained. Instead, the fourth x-ray image 440 may be obtained based on the lower dosage and may indicate a further motion of the patient based on a difference between the fourth x-ray image 440 and the first image 410. The difference may exceed the threshold difference. As such, the tracking operation may switch from obtaining lower dosage x-ray images to obtaining another higher dosage x-ray image. For example, the motion x-ray image 450 may be obtained to more accurately determine how much the patient has moved or shifted from the initial position represented by the first x-ray image 410. Subsequently, the treatment delivery may be modified. The tracking operation may correspond to image registration.

Figure 5A:
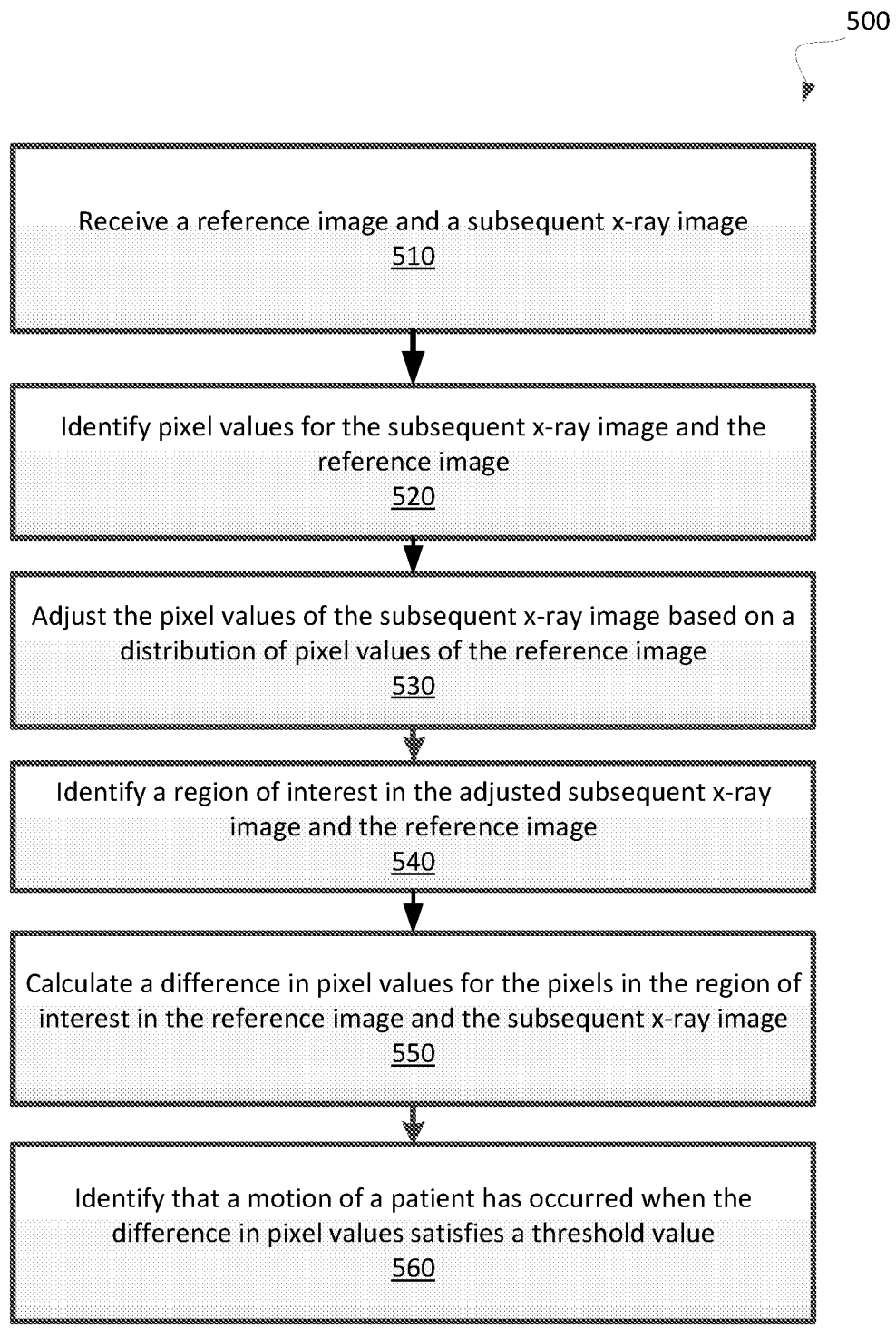
FIG. 5A is a flowchart of an example method to modify at least one of a reference image or a low dose x-ray image to normalize the images in accordance with some embodiments of the present disclosure.

FIG. 5A is an example method 500 to modify at least one of a reference image or a low dose x-ray image to normalize the images. In general, the method 500 may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the method 500 may be performed by processing logic of the radiation treatment system 100 of FIG. 1.

As shown in FIG. 5A, the method 500 may begin with the processing logic receiving a reference image and a subsequent x-ray image (block 510). For example, the subsequent x-ray image may be received after obtaining the reference image as previously described. The processing logic may further identify pixel values for the subsequent x-ray image and the reference image (block 520). A pixel value may represent a brightness or intensity of the corresponding pixel. For example, each of the reference x-ray image and the subsequent image may be greyscale x-ray images where the pixel value may represent the intensity of the corresponding pixel so that a lower value is more black in color than a pixel value of higher value which may be more white in color. In some embodiments, a distribution of the pixel values for each of the images may be determined. For example, a histogram may represent the distribution of pixel values for a respective image. The histogram may thus identify a number of pixels that are assigned a particular pixel value for a particular image. In some embodiments, the distribution of the pixel values may correspond to a distribution of a particular region for each of the images. For example, a first distribution of pixel values for a region (e.g., an outline of a skull of the patient) of the reference image may be identified and a second distribution of pixel values for the subsequent x-ray image at the same area corresponding to the region of the reference image may be identified.

The processing logic may further adjust the pixel values of the subsequent x-ray image based on a distribution of pixel values of the reference image (block 530). For example, the pixel values of the subsequent x-ray image may be changed so that the distribution of pixel values of the subsequent x-ray image matches or approximates the distribution of pixel values of the reference image. In some embodiments, pixel values of the subsequent x-ray image may be lowered or increased based on the distribution of pixel values of the reference image. In the same or alternative embodiments, the pixel values of the reference image may be adjusted based on a distribution of pixel values of the subsequent x-ray image. The processing logic may further identify a region of interest in the adjusted subsequent x-ray image and the reference image (block 540). For example, a feature of a patient may be identified at an area of the reference image and the same area on the subsequent x-ray image may be identified. The processing logic may further calculate a difference in pixel values for the pixels in the region of interest in the reference image and the subsequent x-ray image (block 550). For example, an average difference in pixel values in the region of interest in the images may be calculated. The average difference may be the difference between the average pixel intensity value of the region of interest in the reference image and the average pixel intensity value of the region of interest in the subsequent x-ray image. The processing logic may further identify that a motion has occurred when the difference in pixel values satisfies a threshold value (block 560). For example, when the average of the difference in pixel values equals to or exceeds a threshold value, then the motion may be determined to have occurred. In some embodiments, the motion of the patient may be detected as occurring based on a similarity measure threshold value. For example, the reference image and the subsequent x-ray image may be used in conjunction with a image similarity measure. Examples of such an image similarity measure include, but are not limited to, sum of squared difference, sum of absolute difference, cross-correlation, normalized cross-correlation, mutual information, etc. The output of the similarity measure may be a similarity value. If the similarity value exceeds the similarity measure threshold value, then the reference image and the subsequent x-ray image may be considered to be sufficiently different so that the motion is identifying as having occurred. Otherwise, if the similarity value does not exceed the similarity measure threshold value, then the motion may not be identified as having occurred.

Although aspects of the present disclosure refer to an x-ray imager being used to generate the x-ray images, other components may be used to generate an image for the purposes of detecting a motion of a target of a patient. For example, optical cameras, ultrasound probes, etc. Thus, various motion sensors may be used to generate images and to detect a motion of a target of the patient based on a difference between generated images.

Figure 5B:
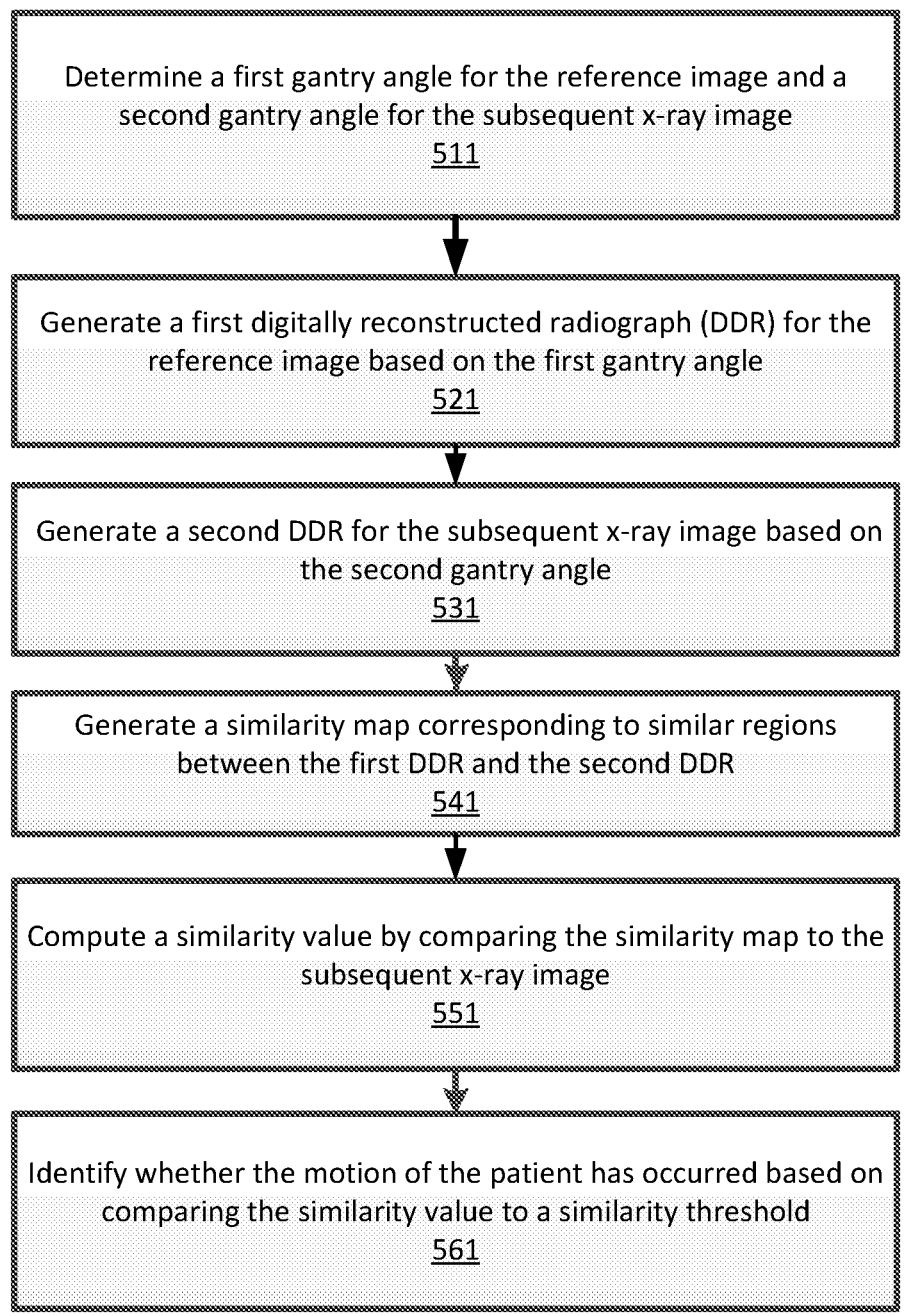
FIG. 5B is a flowchart of a first example method to determine a difference between a reference image and a low dose x-ray image in accordance with some embodiments of the present disclosure.

FIG. 5B is a flowchart of a first example method 501 to determine a difference between a reference image and a low dose x-ray image in accordance with some embodiments of the present disclosure. In general, the method 501 may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the method 501 may be performed by processing logic of the radiation treatment system 100 of FIG. 1. In one embodiment, method 501 may be an extension of method 500 of FIG. 5A.

As shown in FIG. 5B, the method 501 may begin with the processing logic determining a first gantry angle for the reference image and a second gantry angle for the subsequent x-ray image at block 511. In one embodiment, the first and second gantry angles are the same angle. In another embodiment, the first and second gantry angles are two different angles. At block 521, processing logic generates a first digitally reconstructed radiograph (DRR) for the reference image based on the first gantry angle, and at block 531*m* processing logic generates a second DRR for the subsequent x-ray image based on the second gantry angle. Processing logic at block 541 generates a similarity map corresponding to similar regions between the first DRR and the second DRR. For example, the similarity map may identify the regions in the first DRR and the second DRR that are the same (or substantially the same). In another embodiment, the similarity map associates a first position in the first DRR to a second position in the second DRR, where the first and second positions in the respective DRRs correspond to the regions in the first DRR and the second DRR that are the same (or substantially the same).

At block 551, processing logic computes a similarity value by comparing the similarity map to the subsequent x-ray image. In one embodiment, the similarity value corresponds to the level in which the similarity map matched the subsequent x-ray image. The value may be any number in a defined range of numbers (e.g., 0-100). At block 561, processing logic identifies whether the motion of the patient has occurred based on comparing the similarity value to a similarity threshold. In one embodiment, the similarity threshold may be a value on the similarity value scale. In one embodiment, a similarity value below (or equal to) the similarity threshold means that motion of the patient has not occurred (or an amount of motion less than the defined threshold has occurred). A similarity value above (or equal to, in some cases) the similarity threshold may indicate that motion of the patient has occurred (or an amount of motion more than the defined threshold has occurred. In one embodiment, if motion has occurred, processing logic may initiate a correction procedure, as described herein.

Figure 5C:
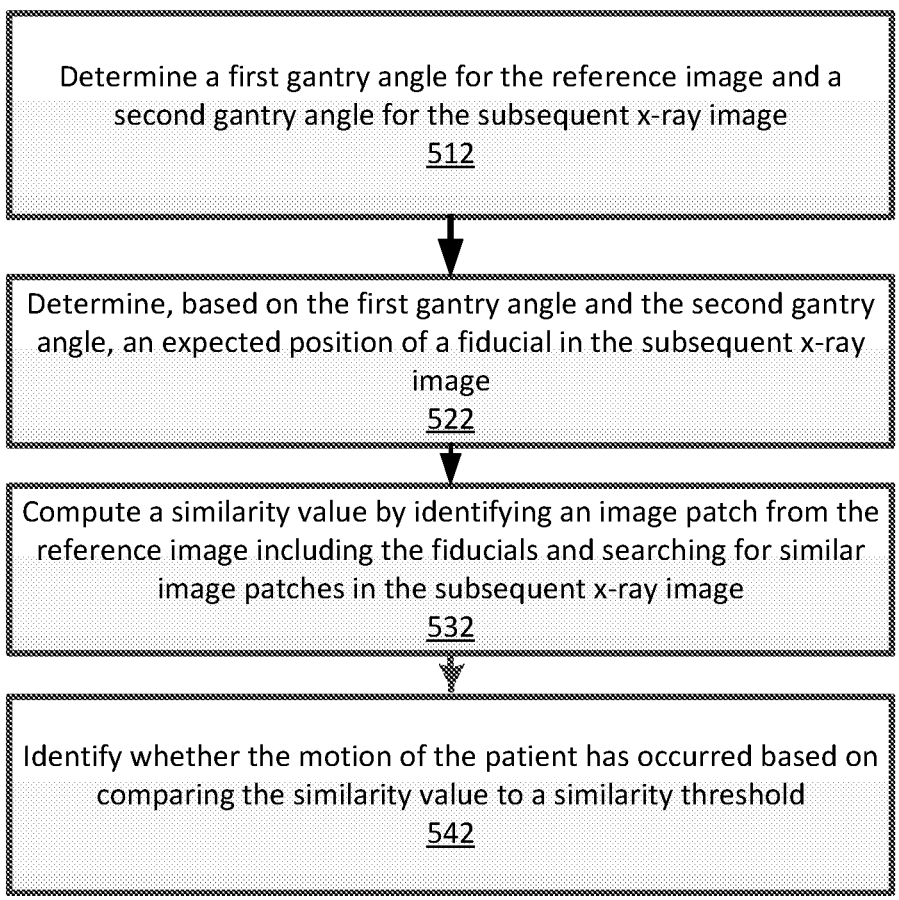
FIG. 5C is a flowchart of a second example method to determine a difference between a reference image and a low dose x-ray image in accordance with some embodiments of the present disclosure.

FIG. 5C is a flowchart of a second example method 502 to determine a difference between a reference image and a low dose x-ray image in accordance with some embodiments of the present disclosure. In general, the method 502 may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the method 502 may be performed by processing logic of the radiation treatment system 100 of FIG. 1. In one embodiment, method 502 may be an extension of method 500 of FIG. 5A.

As shown in FIG. 5B, the method 501 may begin with the processing logic determining a first gantry angle for the reference image and a second gantry angle for the subsequent x-ray image at block 512. In one embodiment, the first and gantry angles are the same angle. In another embodiment, the first and second gantry angles are two different angles. At block 522, processing logic determines, based on the first gantry angle and the second gantry angle, an expected position of a fiducial in the subsequent x-ray image. In one embodiment, a fiducial is any tracking object identified in an image. In another embodiment a fiducial is a specially deposited (e.g., implanted) object (or objects) locatable in an x-ray (or via other types imaging systems), specifically deposited to aid in the tracking of a patient.

At block 532, processing logic computes a similarity value by identifying an image patch from the reference image including the fiducials and searching for similar image patches in the subsequent x-ray image. At block 542, processing logic identifies whether the motion of the patient has occurred based on comparing the similarity value to a similarity threshold. As described herein, in one embodiment the similarity threshold may be a value on the similarity value scale. In one embodiment, a similarity value below (or equal to) the similarity threshold means that motion of the patient has not occurred (or an amount of motion less than the defined threshold has occurred). A similarity value above (or equal to, in some cases) the similarity threshold may indicate that motion of the patient has occurred (or an amount of motion more than the defined threshold has occurred. In one embodiment, if motion has occurred, processing logic may initiate a correction procedure, as described herein.

Figure 6:
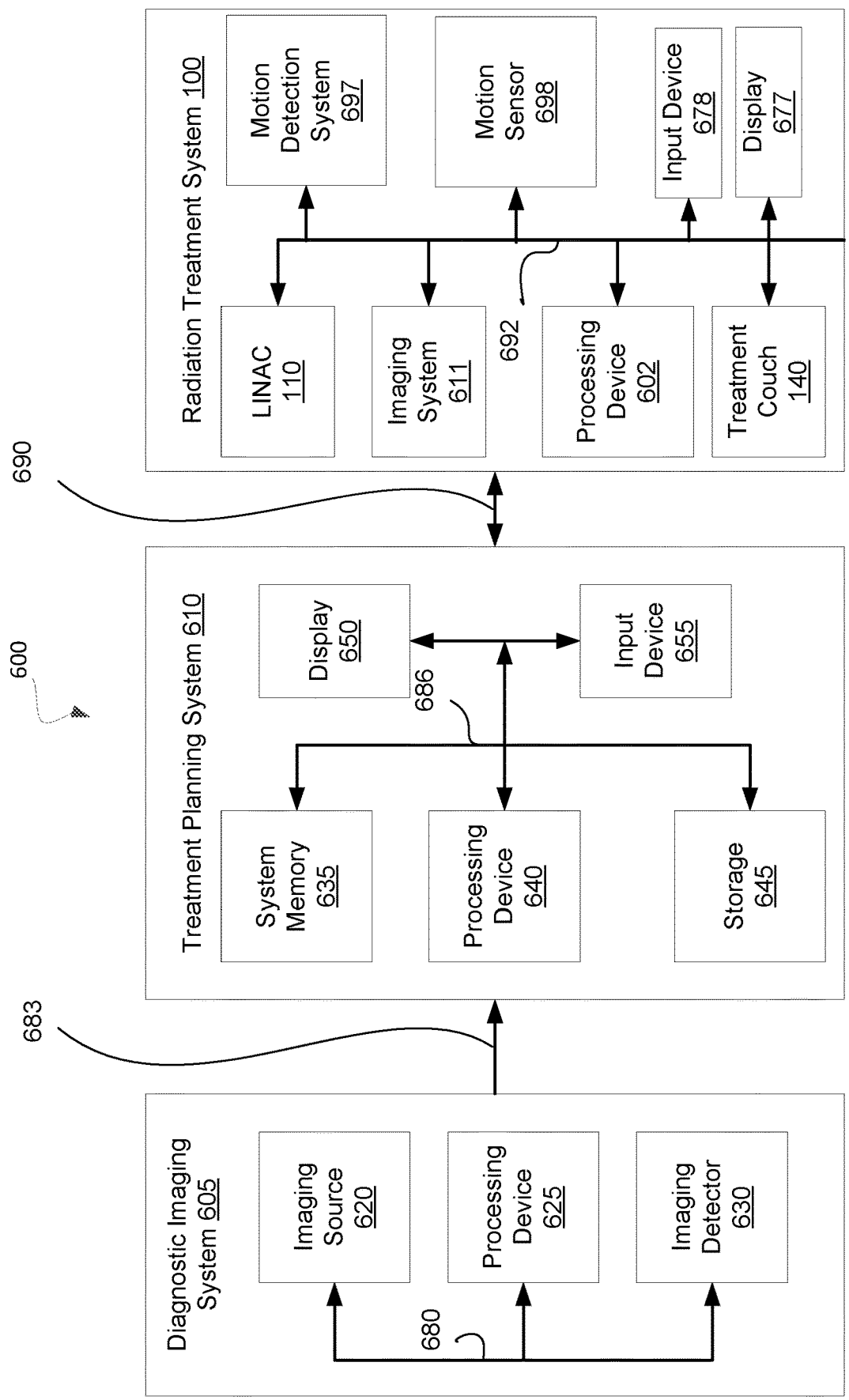
FIG. 6 illustrates a system that may be used in the generating of the performing of radiation treatment in which some embodiments of the disclosure may operate.

FIG. 6 illustrates an example machine of a computer system 600 within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 600 includes a processing device 602, a main memory 604 (e.g., read-only memory (ROM), flash memory, dynamic random access memory (DRAM) such as synchronous DRAM (SDRAM) or Rambus DRAM (RDRAM), etc.), a static memory 606 (e.g., flash memory, static random access memory (SRAM), etc.), and a data storage device 618, which communicate with each other via a bus 630.

Processing device 602 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 602 may also be one or more special-purpose processing devices such as an application specific integrated circuit (ASIC), a field programmable gate array (FPGA), a digital signal processor (DSP), network processor, or the like. The processing device 602 is configured to execute instructions 626 for performing the operations and steps discussed herein.

The computer system 600 may further include a network interface device 608 to communicate over the network 620. The computer system 600 also may include a video display unit 610 (e.g., a liquid crystal display (LCD) or a cathode ray tube (CRT)), an alphanumeric input device 612 (e.g., a keyboard), a cursor control device 614 (e.g., a mouse), a graphics processing unit 622, a signal generation device 616 (e.g., a speaker), graphics processing unit 622, video processing unit 628, and audio processing unit 632.

The data storage device 618 may include a machine-readable storage medium 624 (also known as a computer-readable medium) on which is stored one or more sets of instructions or software 626 embodying any one or more of the methodologies or functions described herein. The instructions 626 may also reside, completely or at least partially, within the main memory 604 and/or within the processing device 602 during execution thereof by the computer system 600, the main memory 604 and the processing device 602 also constituting machine-readable storage media.

In one implementation, the instructions 626 include an x-ray motion component 699 to implement functionality corresponding to the disclosure herein. While the machine-readable storage medium 624 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Figure 7:
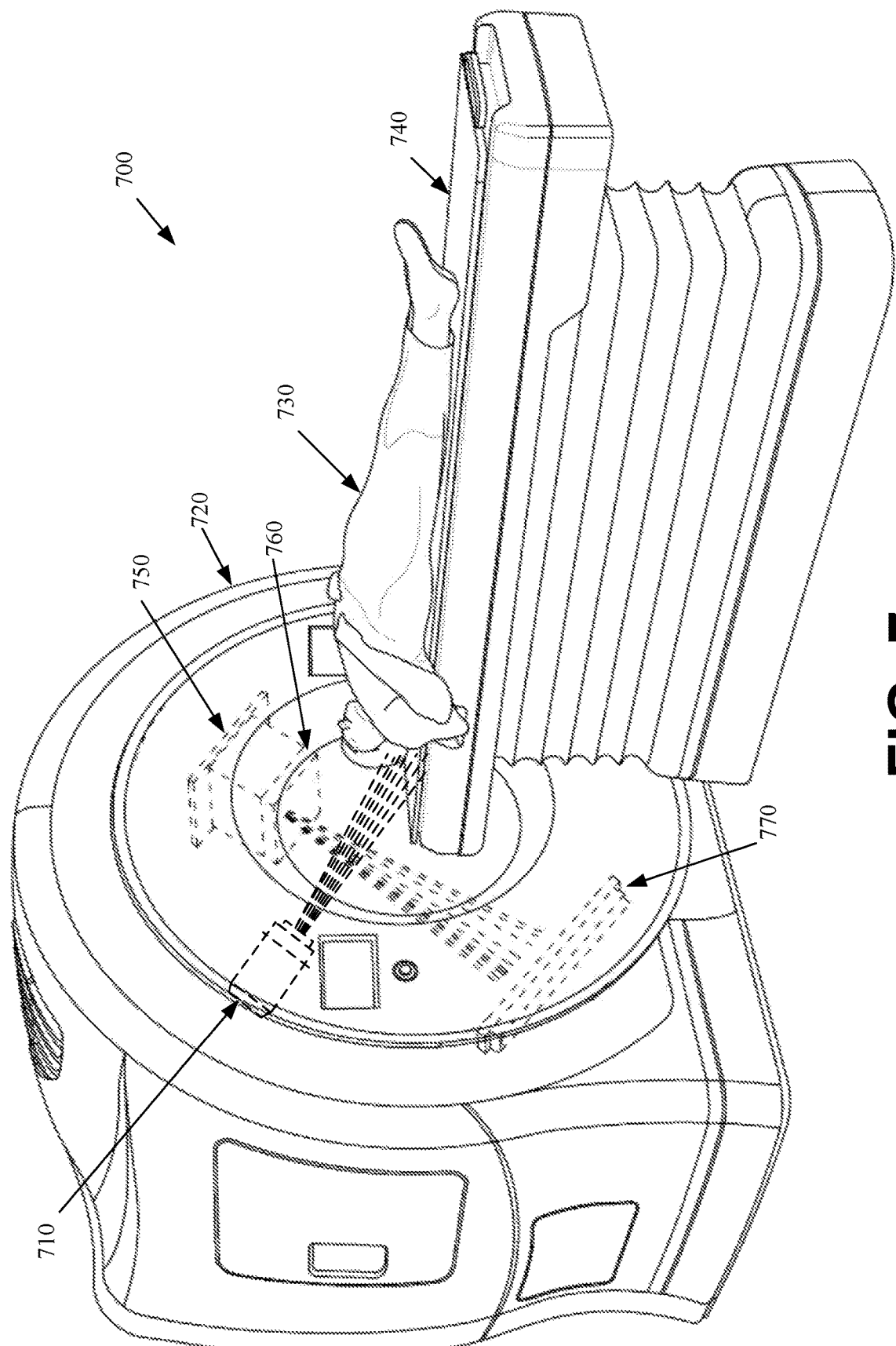
FIG. 7 illustrates a helical radiation delivery system in accordance with embodiments of the present disclosure.

FIG. 7 illustrates a helical radiation delivery system 700 in accordance with embodiments of the present disclosure. The helical radiation delivery system 700 may include a linear accelerator (LINAC) 710 mounted to a ring gantry 720. The LINAC 710 may be used to generate a narrow intensity modulated pencil beam (i.e., treatment beam) by directing an electron beam towards an x-ray emitting target. The treatment beam may deliver radiation to a target region (i.e., a tumor). The ring gantry 720 generally has a toroidal shape in which the patient 730 extends through a bore of the ring/toroid and the LINAC 710 is mounted on the perimeter of the ring and rotates about the axis passing through the center to irradiate a target region with beams delivered from one or more angles around the patient. During treatment, the patient 730 may be simultaneously moved through the bore of the gantry on treatment couch 740.

The helical radiation delivery system 700 includes a treatment imaging system, which may include a kV imaging source 750 and an x-ray detector 770. The kV imaging source 750 may be used to generate x-ray images of a ROI of patient 730 by directing a sequence of x-ray beams at the ROI which are incident on the x-ray detector 770 opposite the kV imaging source 750 to image the patient 730 for setup and generate in-treatment images. The treatment imaging system may further include a collimator 760. In one embodiment, the collimator 760 may be a variable aperture collimator. In another embodiment, the collimator 760 may be a multi-leaf collimator (MLC). The MLC includes a housing that houses multiple leaves that are movable to adjust an aperture of the MLC to enable shaping of an imaging x-ray beam. In another embodiment, the variable aperture collimator 760 may be an iris collimator containing trapezoidal blocks that move along a frame in a manner similar to a camera iris to produce an aperture of variable size that enables shaping of the imaging x-ray beam. The kV imaging source 750 and the x-ray detector 770 may be mounted orthogonally relative to the LINAC 710 (e.g., separated by 90 degrees) on the ring gantry 720 and may be aligned to project an imaging x-ray beam at a target region and to illuminate an imaging plane of detector 770 after passing through the patient 130. In some embodiments, the LINAC 710 and/or the kV imaging source 750 may be mounted to a C-arm gantry in a cantilever-like manner, which rotates the LINAC 710 and kV imaging source 750 about the axis passing through the isocenter. Aspects of the present disclosure may further be used in other such systems such as a gantry-based LINAC system, static imaging systems associated with radiation therapy and radiosurgery, proton therapy systems using an integrated image guidance, interventional radiology and intraoperative x-ray imaging systems, etc.

Figure 8:
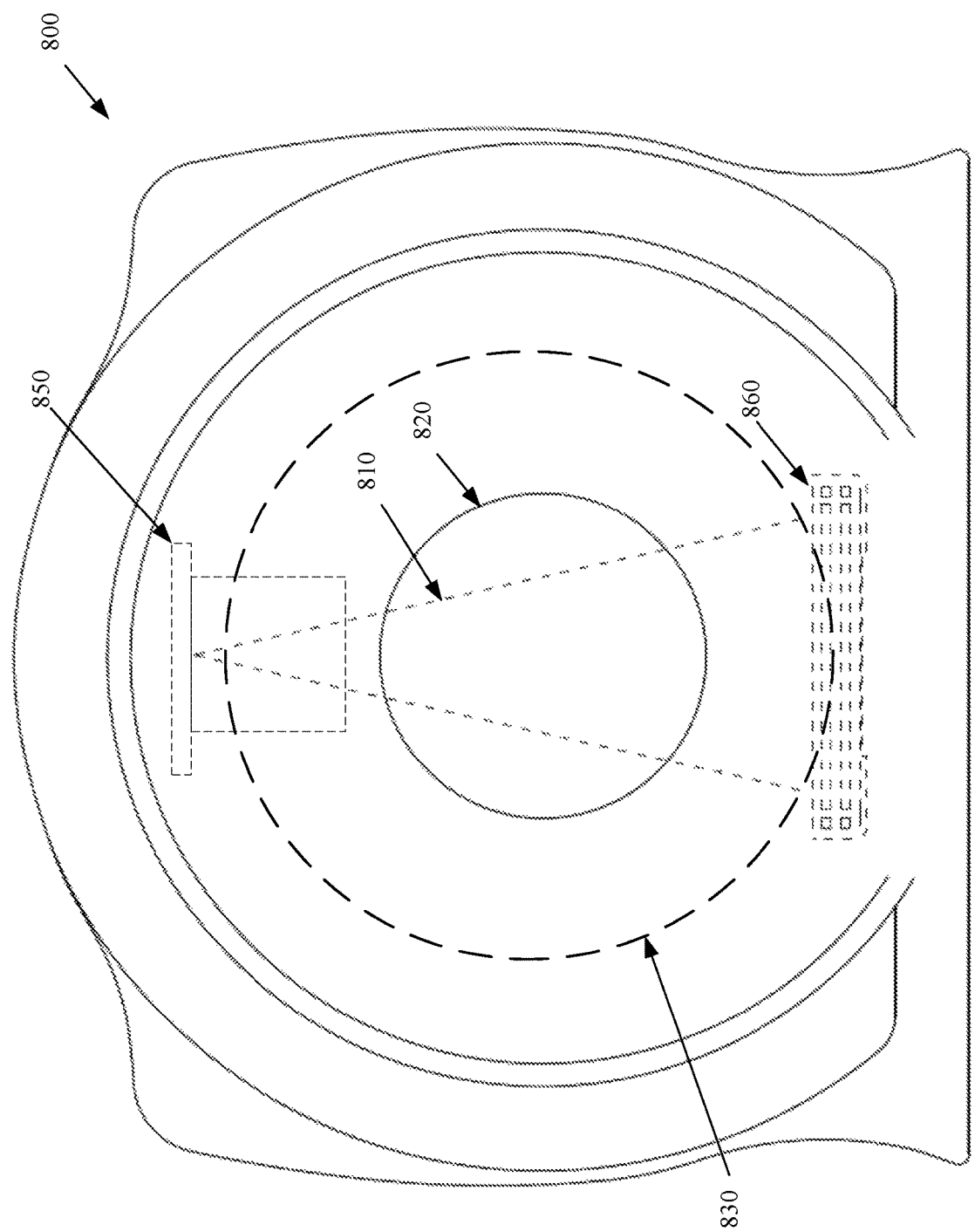
FIG. 8 illustrates a cross-section of the helical radiation treatment delivery system in which some embodiments of the disclosure may operate.

FIG. 8 is a cross-section 800 of the helical radiation delivery system 700 of FIG. 7. As previously discussed, the kV imaging source 850 projects an imaging x-ray beam 810 through the bore 820 of the treatment system which illuminates the imaging plane of x-ray detector 870 after passing through a patient. The kV imaging source 850 and x-ray detector 870 may rotate along a circular track 830 of the ring gantry 820 around the bore 820 of the treatment system to generate x-ray images of a target region from multiple angles.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various general purpose systems may be used with programs in accordance with the teachings herein, or it may prove convenient to construct a more specialized apparatus to perform the method. The structure for a variety of these systems will appear as set forth in the description below. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A method comprising:
   generating a reference image of a patient;
   generating a subsequent x-ray image of the patient after the generating of the reference image, the subsequent x-ray image being associated with a low dosage;
   determining, by a processing device, a difference between the reference image and the subsequent x-ray image that is associated with the low dosage; and
   identifying whether a motion of the patient has occurred based on the determined difference.

2. The method of claim 1, further comprising:
   in response to identifying that the motion of the patient has occurred, generating a motion x-ray image that is associated with a second dosage that is higher than the low dosage associated with the subsequent x-ray image;
   performing image registration between the reference image and the motion x-ray image to estimate an amount of the motion of the patient that has occurred; and
   modifying a medical procedure for the patient based on the amount of the motion of the patient that has occurred.

3. The method of claim 1, wherein identifying whether the motion of the patient has occurred comprises:
   determining a similarity value between the reference image and the subsequent x-ray image based on a difference in pixel values between the reference image and the subsequent x-ray image that is associated with the low dosage, the motion being identified as occurring when the similarity value exceeds a threshold value and the motion not being identified as occurring when the similarity value does not exceed the threshold value.

4. The method of claim 1, wherein determining the difference between the reference image and the subsequent x-ray image comprises:
   determining a difference in pixel values between the reference image and the subsequent x-ray image that is associated with the low dosage; and
   normalizing pixel values of the subsequent x-ray image with the reference image, the normalizing of the pixel values being based on changing pixel values of the subsequent x-ray image or the reference image based on a distribution of pixel values of the reference image or the subsequent x-ray image.

5. The method of claim 1, wherein determining the difference between the reference image and the subsequent x-ray image comprises:
   determining a first gantry angle for the reference image and a second gantry angle for the subsequent x-ray image;
   generating a first digitally reconstructed radiograph (DRR) for the reference image based on the first gantry angle;
   generating a second DRR for the subsequent x-ray image based on the second gantry angle;
   generating a similarity map corresponding to similar regions between the first DRR and the second DRR;
   computing a similarity value by comparing the similarity map to the subsequent x-ray image; and
   identifying whether the motion of the patient has occurred based on comparing the similarity value to a similarity threshold.

6. The method of claim 1, wherein determining the difference between the reference image and the subsequent x-ray image comprises:
   determining a first gantry angle for the reference image and a second gantry angle for the subsequent x-ray image;
   determining, based on the first gantry angle and the second gantry angle, an expected position of a fiducial in the subsequent x-ray image;
   computing a similarity value by identifying an image patch from the reference image including the fiducials and searching for similar image patches in the subsequent x-ray image; and
   identifying whether the motion of the patient has occurred based on comparing the similarity value to a similarity threshold.

7. The method of claim 2, wherein the reference image, the subsequent x-ray image, and the motion x-ray image are generated by an x-ray imaging source of a helical radiation delivery system or by one or more x-ray imaging sources at different positions with respect to the patient.

8. The method of claim 1, further comprising:
   in response to identifying that the motion of the patient has not occurred, generating another subsequent x-ray image that is associated with the low dosage at a time period after generating the subsequent x-ray image.

9. The method of claim 1, further comprising:
   performing a tracking operation associated with the patient based on identifying that the motion of the patient has occurred to modify a radiation treatment delivery for the patient.

10. The method of claim 1, wherein the reference image is an x-ray image.

11. The method of claim 1, wherein the reference image is a digitally reconstructed radiograph.

12. The method of claim 1, wherein the reference image and the subsequent x-ray image being from nearby beam positions corresponding to known movement of a treatment couch or an imaging gantry.

13. A system comprising:
    a memory;
    a motion sensor; and
    a processing device, operatively coupled with the memory, to:
      receive a reference image of a patient from the motion sensor;
      receive a subsequent x-ray image of the patient from the motion sensor after the receiving of the reference image, the subsequent x-ray image being associated with a low dosage;
      determine a difference between the reference image and the subsequent x-ray image that is associated with the low dosage; and
      identify whether a motion of the patient has occurred based on the determined difference.

14. The system of claim 13, wherein the processing device is further to:
- in response to identifying that the motion of the patient has occurred, generate a motion x-ray image that is associated with a second dosage that is higher than the low dosage associated with the subsequent x-ray image;
- perform image registration between the reference image and the motion x-ray image to estimate an amount of the motion of the patient that has occurred; and
- modify a medical procedure for the patient based on the amount of the motion of the patient that has occurred.

15. The system of claim 13, wherein to identify whether the motion of the patient has occurred, the processing device is further to:
- determine a similarity value between the reference image and the subsequent x-ray image based on a difference in pixel values between the reference image and the subsequent x-ray image that is associated with the low dosage, the motion being identified as occurring when the similarity value exceeds a threshold value and the motion not being identified as occurring when the similarity value does not exceed the threshold value.

16. The system of claim 13, wherein to determine the difference between the reference image and the subsequent x-ray image, the processing device is further to:
- determine a difference in pixel values between the reference image and the subsequent x-ray image that is associated with the low dosage; and
- normalize pixel values of the subsequent x-ray image with the reference image, the normalizing of the pixel values being based on changing pixel values of the subsequent x-ray image or the reference image based on a distribution of pixel values of the reference image or the subsequent x-ray image.

17. The system of claim 14, wherein the reference image, the subsequent x-ray image, and the motion x-ray image are generated by an x-ray imaging source of a helical radiation delivery system or by one or more x-ray imaging sources at different positions with respect to the patient.

18. The system of claim 13, wherein the processing device is further to:
- in response to identifying that the motion of the patient has not occurred, generate another subsequent x-ray image that is associated with the low dosage at a time period after generating the subsequent x-ray image.

19. The system of claim 13, wherein the processing device is further to:
- perform a tracking operation associated with the patient based on identifying that the motion of the patient has occurred to modify a radiation treatment delivery for the patient.

20. A non-transitory computer readable medium comprising instructions that, when executed by a processing device, cause the processing device to:
- generate a reference image of a patient;
- generate a subsequent x-ray image of the patient after the generating of the reference image, the subsequent x-ray image being associated with a low dosage;
- determine, by the processing device, a difference between the reference image and the subsequent x-ray image that is associated with the low dosage; and
- identify whether a motion of the patient has occurred based on the determined difference.

21. The non-transitory computer readable medium of claim 20, wherein the processing device is further to:
- in response to identifying that the motion of the patient has occurred, generate a motion x-ray image that is associated with a second dosage that is higher than the low dosage associated with the subsequent x-ray image;
- perform image registration between the reference image and the motion x-ray image to estimate an amount of the motion of the patient that has occurred; and
- modify a medical procedure for the patient based on the amount of the motion of the patient that has occurred.

22. The non-transitory computer readable medium of claim 20, wherein to identify whether the motion of the patient has occurred, the processing device is further to:
- determine a similarity value between the reference image and the subsequent x-ray image based on a difference in pixel values between the reference image and the subsequent x-ray image that is associated with the low dosage, the motion being identified as occurring when the similarity value exceeds a threshold value and the motion not being identified as occurring when the similarity value does not exceed the threshold value.

23. The non-transitory computer readable medium of claim 20, wherein to determine the difference between the reference image and the subsequent x-ray image, the processing device is further to:
- determine a difference in pixel values between the reference image and the subsequent x-ray image that is associated with the low dosage; and
- normalize pixel values of the subsequent x-ray image with the reference image, the normalizing of the pixel values being based on changing pixel values of the subsequent x-ray image or the reference image based on a distribution of pixel values of the reference image or the subsequent x-ray image.

24. The non-transitory computer readable medium of claim 21, wherein the reference image, the subsequent x-ray image, and the motion x-ray image are generated by an x-ray imaging source of a helical radiation delivery system or by one or more x-ray imaging sources at different positions with respect to the patient.

25. The non-transitory computer readable medium of claim 20, wherein the processing device is further to:
- in response to identifying that the motion of the patient has not occurred, generate another subsequent x-ray image that is associated with the low dosage at a time period after generating the subsequent x-ray image.

26. The non-transitory computer readable medium of claim 20, wherein the reference image and the subsequent x-ray image being from nearby beam positions corresponding to know movement of a treatment couch or an imaging gantry.

* * * * *